United States Patent [19]

Müller

[11] Patent Number: 4,784,662

[45] Date of Patent: Nov. 15, 1988

[54] ARTIFICIAL HIP JOINT

[75] Inventor: Maurice E. Müller, Bern, Switzerland

[73] Assignees: Sulzer Brothers Limited, Winterthur; Protek AG, Berne, both of Switzerland

[21] Appl. No.: 924,917

[22] Filed: Oct. 29, 1986

[30] Foreign Application Priority Data

Nov. 18, 1985 [CH] Switzerland ............... 4914/85

[51] Int. Cl.$^4$ ................. A61F 2/34; A61F 2/30
[52] U.S. Cl. ............................. 623/22; 623/18
[58] Field of Search ............. 623/16, 18, 20, 21, 623/22, 23

[56] References Cited

U.S. PATENT DOCUMENTS

| 4,159,544 | 7/1979 | Termanini | 623/22 |
| 4,318,627 | 3/1982 | Morin | 463/133 |
| 4,566,138 | 1/1986 | Lewis et al. | 623/22 |

FOREIGN PATENT DOCUMENTS

| 0119321 | 9/1984 | European Pat. Off. | 623/22 |
| 3322978 | 1/1985 | Fed. Rep. of Germany | 623/22 |
| 3341723 | 3/1985 | Fed. Rep. of Germany | 623/22 |

Primary Examiner—Richard J. Apley
Assistant Examiner—David J. Isabella
Attorney, Agent, or Firm—Kenyon & Kenyon

[57] ABSTRACT

The socket is made with a bowl having a spherical cap in the polar region and a part-spherical section which extends from the spherical cap on a larger diameter. The two sections join together at a distance from the top of the bowl socket which is ⅓ the diameter of the spherical cap while the diameter of the part-spherical section is from 1.02 to 1.10 times the diameter of the spherical cap. The diameters of the spherical cap and the part-spherical section intersect the axis of symmetry of the socket body, one on the equatorial plane and the other below the equatorial plane.

6 Claims, 1 Drawing Sheet

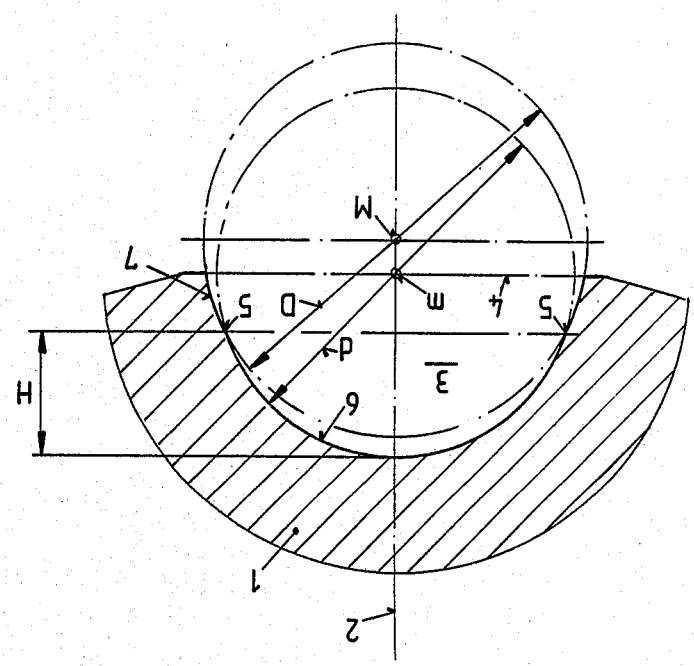

ARTIFICIAL HIP JOINT

This invention relates to an artificial hip joint socket.

As is known, various types of artificial hip joint sockets have been provided for receiving spherical joint heads. In some cases, the sockets have been made with bowls of spherical shape in order to receive a similarly shaped joint head. However, such sockets, particularly if the sockets are relatively soft, i.e. if the elastisity of the of the sockets approach the elastisity of the pelvis, on the one hand, experience a brake drum effect which intensifies in the course of time due to, if minimal, abrasion. On the other hand, there is a danger of luxation of the joint head out of the socket bowl when the joint is bent to a great degree, for example when sitting.

A "brake drum effect", as is known, is a wedging in of a joint head wherein deformations of the socket and/or socket bowl occur under which the free edge of the socket flaps and folds like the arms of a grip. If the socket bowls are made relatively flat in order to reduce the grip effect, there is an increased susceptibility of the joint prothesis to luxations of the joint head out of the socket bowl.

In order to diminish these above effects, it has been known, for example from Swiss Pat. No. 593,054, to form the bowl of a hip joint socket from other than a spherical surface, namely from arc sections, the centers of which are spaced apart. To this end, the socket bowl is a rotation surface, the generating curve of which is composed of two arc portions of equal radii having centers aligned in an equatorial plane and horizontally spaced along the plane from the axis of rotation. However, it has been found in practice that a wedging in of the joint head cannot always be prevented to a sufficient degree, especially after a prolonge "running time".

Accordingly, it is an object of the invention to head in the socket bowl is avoided without an increase in the danger of luxations.

It is another object of the invention to provide a hip joint socket which eliminates the brake drum effect.

It is another object of the invention to provide a hip joint socket having an improved bearing surface for a spherical joint head.

It is another object of the invention to reduce the risk of a luxation of a joint head from a hip joint socket.

Briefly, the invention provides an artificial hip has a socket bowl disposed in symmetric relation about a longitudinal axis with a spherical section at a polar region of a first diameter to define a spherical cap of a height equal to ⅓ of the diameter. In addition, the from the spherical section on a diameter greater than the diameter of the spherical section.

In accordance with the invention, the socket bowl extends to a plane, i.e. an equatorial plane, extending perpendicularly of the axis of symmetry and extending through a point of intersection of the diameter of the spherical section with the axis of symmetry. In addition, the diameter of the part-spherical section intersects the longitudinal axis of symmetry at a second point on a side of the equatorial plane which is opposite to the spherical cap.

Experimentally, it has been found favorable if the diameter of the part-spherical section is from 1.02 to 1.10 times the diameter of the spherical cap section. Further, the absolute diameter of the spherical cap section is made 0.5 millimeters greater than the diameter of the spherical joint head which is to be received in the socket bowl.

Limiting the adaption of the bowl surface to the joint head to the polar region results in a limitation of the bearing surface for the joint head during "normal" joint movements to this polar region. Thus, a "grip movement" of the "edge" of the region is greatly reduced because of the much shorter lever arms as compared with an equatorial edge. In the case of luxation of a joint head under strong flexture of the joint, the part-spherical section brings about a guiding of the joint head so that the luxation danger is reduced. The greater diameter of this part-spherical section results, at the same time, in an increased play between the joint head and the socket bowl in the region near the equatorial plane. Hence, an additional reduction of the danger of clamping is effected.

The hip joint socket ma be made of the known implant materials. However, preferred materials are polyethylene, or titanium or a titanium alloy. Further, the hip joint socket may be provided with a structured outer surface in order to improve implantation in a bone or may be embedded in an outer ring or an outer bowl.

These and other objects and advantages of the invention will become more apparent from the following detailed description taken in conjunction with the drawing wherein:

The Figure illustrates a cross-sectional view of an artificial hip joint socket constructed in accordance with the invention.

Referring to the drawing, the artificial hip joint socket is shaped for receiving a spherical joint head (not shown). As indicated, the socket has a body 1 with a socket bowl 3 disposed in symmetric relation about a longitudinal axis 2. In this regard, the axis 2 is also an axis of symmetry for the outer surface of the socket body 1.

The socket bowl 3 has a spherical section at a polar region of a first diameter d in order to define a spherical cap 6 of a height H which is equal to ⅓ of the diameter d. As indicated, the diameter d intersects the longitudinal axis of symmetry 2 at a point m on an equatorial plane 4, i.e. a plane which extends perpendicularly of the axis of symmetry 2 and which extends through the point of intersection m of the diameter d with the axis 2. The absolute value of the diameter d of the spherical cap 6 corresponds to the diameter of a joint head which is to be received plus a play of 0.5 millimeters.

The socket bowl 3 also has an annular part-spherical section 7 which extends from the spherical cap section 6 on a second diameter D which is greater than the diameter d of the spherical cap section 6. As illustrated, the part-spherical section 7 begins at a distance H from the summit (i.e. top) of the socket bowl 3 at points 5 on a plane of discontinuity with the spherical cap 6 and extends to the equatorial plane 4. The diameter D of the part-spherical section 7 intersects the longitudinal axis of the symmetry 2 at a point M on a side of the equatorial plane 4 which is opposite the spherical cap 6. In the present example, the diameter D is 1.065 times the diameter d of the spherical cap 6.

Of note, with the position of the discontinuity of the part-spherical section 7 from the spherical cap 6 at a known distance H from the summit of the socket bowl 3 and with the known value of the diameter D, the position of the point M on the axis of rotation 2 can be easily determined.

The socket body 1 may also be provided on the outer surface with a structure to improve implantation or adhesion in a bone (not shown) or may itself serve as an inner bowl of a two-bowl socket.

When in use, the hip joint socket 1 receives the spherical head of a joint on the spherical cap 6. At this time, the part-spherical section 7 is slightly spaced from the surface of the joint head. Thus, the joint head bears only on the polar region of the socket bowl 3 with little play due to the differences in diameter of the joint head and polar region. This the joint be subsequently flexed to a great degree, for example during sitting, the part-spherical section 7 permits the joint head to be guided so as to reduce the risk of a luxation.

What is claimed is:

1. An artificial hip joint socket for receiving a joint head, said socket having a socket bowl disposed in symmetric relation about a longitudinal axis with a spherical section at a polar region of a first diameter to define a spherical cap of a height equal to ⅓ said first diameter, and an annular part-spherical section extending from said spherical section on a second diameter greater than said first diameter.

2. An artificial hip joint socket as set forth in claim 1 wherein said socket bowl extends to an equatorial plane of said spherical section, said first diameter intersects said longitudinal axis of symmetry at a first point on said equatorial plane and said second diameter intersects said longitudinal axis at a second point on a side of said equatorial plane opposite said spherical cap.

3. An artificial hip joint socket as set forth in claim 1 wherein said second diameter is from 1.02 to 1.10 times said first diameter.

4. An artificial hip joint as set forth in claim 3 wherein said first diameter is 0.5 millimeters greater than the diameter of a spherical joint head to be received in said socket bowl.

5. An artificial hip joint as set forth in claim 1 wherein said socket bowl extends to a plane extending perpendicularly of said axis and extending through a point of intersection of said first diameter with said axis.

6. An artificial hip joint as set forth in claim 5 wherein said part spherical section extends to said plane.

* * * * *

UNITED STATES PATENT AND TRADEMARK OFFICE
CERTIFICATE OF CORRECTION

PATENT NO. : 4,784,662
DATED : Nov. 15, 1988
INVENTOR(S) : Maurice E. Muller

It is certified that error appears in the above-identified patent and that said Letters Patent is hereby corrected as shown below:

```
Column 1, line 10 "elastisity" should be -elasticity-
Column 1, line 11 cancel "of the" (first occurrence)
Column 1, line 11 "approach" should be -approaches-
Column 1, line 36 "prolonge" should be -prolonged-
Column 1, line 37 "to head" should be -to provide a hip-joint
     socket in which a wedging in of a joint head-
Column 1, line 48 "hip has" should be -hip-joint socket for
     receiving a joint head where the socket has-
Column 1, line 52 "the from" should be -the socket has an annular
     part-sphereical section extending from-
Column 2, line 10 "flexture" should be -flexure-
Column 2, line 18 "ma" should be -may-
Column 3, line 12 "This the" should be -This reduces the danger
of a wedging in of the joint head.  Should the-
```

Signed and Sealed this

Sixth Day of June, 1989

*Attest:*

DONALD J. QUIGG

*Attesting Officer*    *Commissioner of Patents and Trademarks*